United States Patent
Ellis et al.

(10) Patent No.: US 9,102,105 B2
(45) Date of Patent: Aug. 11, 2015

(54) METHOD FOR FORMING AN OCULAR DRUG DELIVERY DEVICE

(75) Inventors: Edward J. Ellis, Lynnfield, MA (US); Jeanne Y. Ellis, Lynnfield, MA (US)

(73) Assignee: VISTA SCIENTIFIC LLC, Andover, MA (US)

( * ) Notice: Subject to any disclaimer, the term of this patent is extended or adjusted under 35 U.S.C. 154(b) by 370 days.

(21) Appl. No.: 13/614,883

(22) Filed: Sep. 13, 2012

(65) Prior Publication Data

US 2013/0062809 A1    Mar. 14, 2013

Related U.S. Application Data

(60) Provisional application No. 61/534,211, filed on Sep. 13, 2011.

(51) Int. Cl.
*B29C 70/70* (2006.01)
*B29L 31/00* (2006.01)

(52) U.S. Cl.
CPC ........... *B29C 70/70* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 3,416,530 A | 12/1968 | Ness | |
| 3,618,604 A | 11/1971 | Ness | |
| 3,630,200 A * | 12/1971 | Higuchi | 424/427 |
| 3,710,796 A * | 1/1973 | Neefe | 424/429 |
| 3,786,812 A * | 1/1974 | Neefe | 424/429 |
| 3,828,777 A | 8/1974 | Ness | |
| 3,845,201 A | 10/1974 | Haddad et al. | |
| 3,867,519 A | 2/1975 | Michaels | |
| 3,960,150 A * | 6/1976 | Hussain et al. | 424/428 |
| 3,961,628 A * | 6/1976 | Arnold | 424/427 |
| 3,962,414 A | 6/1976 | Michaels | |
| 3,963,025 A | 6/1976 | Whitaker et al. | |
| 3,972,995 A * | 8/1976 | Tsuk et al. | 424/435 |
| 3,993,071 A | 11/1976 | Higuchi | |
| 3,995,635 A | 12/1976 | Higuchi | |
| 4,014,335 A | 3/1977 | Arnold | |
| 4,135,514 A | 1/1979 | Zaffaroni et al. | |
| 4,164,559 A | 8/1979 | Miyata et al. | |
| 4,179,497 A | 12/1979 | Cohen et al. | |
| 4,186,184 A | 1/1980 | Zaffaroni | |
| 4,190,642 A | 2/1980 | Ben-Dor | |

(Continued)

FOREIGN PATENT DOCUMENTS

| | | |
|---|---|---|
| EP | 0262893 | 4/1988 |
| EP | 0923918 | 6/1999 |

(Continued)

OTHER PUBLICATIONS

D. Lisa Land, et al.; "Sizes and Shapes of Conjunctival Inserts"; ICLC, vol. 21 Nov./Dec. 1994; pp. 212-217.

(Continued)

*Primary Examiner* — Edmund Lee
(74) *Attorney, Agent, or Firm* — Leason Ellis LLP

(57) ABSTRACT

A method for forming an ocular drug delivery device includes the steps of: (1) forming a drug core containing an active agent, wherein the drug core has a barrier disposed all surfaces thereof except for a drug release surface which is left free of the barrier; (2) forming a drug release membrane over the drug release surface; and (3) forming the remaining portion of the device body by an overcast (overmold) process.

25 Claims, 15 Drawing Sheets

(56) References Cited

U.S. PATENT DOCUMENTS

| | | | |
|---|---|---|---|
| 4,343,787 A | 8/1982 | Katz | |
| 4,592,752 A | 6/1986 | Neefe | |
| 4,655,768 A * | 4/1987 | Marecki et al. | 424/448 |
| 4,730,013 A | 3/1988 | Bondi et al. | |
| 4,863,457 A | 9/1989 | Lee | |
| 5,137,728 A | 8/1992 | Bawa | |
| 5,147,647 A | 9/1992 | Darougar | |
| 5,314,419 A * | 5/1994 | Pelling | 604/294 |
| 5,322,691 A | 6/1994 | Darougar et al. | |
| 5,378,475 A | 1/1995 | Smith et al. | |
| 5,472,436 A | 12/1995 | Fremstad | |
| 5,660,851 A | 8/1997 | Domb | |
| 6,001,386 A * | 12/1999 | Ashton et al. | 424/423 |
| 6,217,896 B1 | 4/2001 | Benjamin | |
| 6,413,245 B1 | 7/2002 | Yaacobi et al. | |
| 6,413,540 B1 * | 7/2002 | Yaacobi | 424/427 |
| 6,416,777 B1 | 7/2002 | Yaacobi | |
| 6,669,950 B2 | 12/2003 | Yaacobi | |
| 6,713,081 B2 * | 3/2004 | Robinson et al. | 424/427 |
| 6,808,719 B2 | 10/2004 | Yaacobi | |
| 6,964,781 B2 | 11/2005 | Brubaker | |
| 6,986,900 B2 | 1/2006 | Yaacobi | |
| 6,991,808 B2 * | 1/2006 | Brubaker et al. | 424/473 |
| 7,094,226 B2 | 8/2006 | Yaacobi | |
| 7,943,162 B2 | 5/2011 | Missel et al. | |
| 8,414,912 B2 * | 4/2013 | Ciolino et al. | 424/429 |
| 8,765,166 B2 * | 7/2014 | Kopczynski et al. | 424/427 |
| 2004/0176749 A1 | 9/2004 | Lohmann | |
| 2004/0219181 A1 | 11/2004 | Viscasillas | |
| 2005/0013845 A1 | 1/2005 | Warren et al. | |
| 2005/0181018 A1 | 8/2005 | Peyman | |
| 2005/0220872 A1 * | 10/2005 | Ozeki | 424/468 |
| 2006/0034929 A1 | 2/2006 | Brubaker | |
| 2008/0107713 A1 * | 5/2008 | Orilla et al. | 424/429 |
| 2008/0145406 A1 | 6/2008 | Asgharian et al. | |
| 2008/0171072 A1 | 7/2008 | Burczynski | |
| 2010/0272777 A1 | 10/2010 | Robinson et al. | |

FOREIGN PATENT DOCUMENTS

| | | |
|---|---|---|
| EP | 1473003 | 11/2004 |
| JP | Hei 6-273702 A | 9/1994 |
| JP | Hei 11-151263 A | 6/1999 |
| WO | WO 01/32140 | 5/2001 |
| WO | WO 03/020172 | 3/2003 |

OTHER PUBLICATIONS

Marco Fabrizio Saettone; :Solid Polymeric Inserts/Disks as Drug Devices; Biopharmaceutics of Ocular Drug Delivery; pp. 61-79 ; 1993.

* cited by examiner

METHOD FOR FORMING AN OCULAR DRUG DELIVERY DEVICE

CROSS-REFERENCE TO RELATED APPLICATION

The present application claims the benefit of U.S. patent application Ser. No. 61/534,211, filed Sep. 13, 2011, which is hereby incorporated by reference in its entirety.

STATEMENT REGARDING FEDERAL SPONSORSHIP

The U.S. Government has a paid-up license in this invention and the right in limited circumstances to require the patent owner to license others on reasonable terms as provided for by the terms of grant #2 R44 EY013479-04 awarded by the National Institutes of Health.

TECHNICAL FIELD

The present invention relates to drug delivery devices and more particularly, relates to a method of making a composite sustained release ocular drug delivery device that includes a drug core positioned adjacent to a surface on the device covered by a thin membrane that is an integral part of the device body.

BACKGROUND

There are a vast number of ways for delivering an active agent, such as a drug, to the body. For example, the active agent can be delivered topically or can be ingested in pill form, etc. In addition, mechanisms for sustained release of the active agent over a predetermined period of time are also known.

One type of drug delivery device is an ocular drug delivery device that delivers an active agent to the eye. The idea of placing a solid device into or near the eye to deliver a drug or a lubricant over time is not new. Most recent scientific interest in this field stems from advances in surgical techniques, pharmacology and pharmacokinetics, as well as the availability of improved polymer systems that can be tailored to the specific needs of ocular drug delivery. For clarity, the distinction should be made between a device that is "inserted into the eye", meaning placed under the eyelids, external to the eyeball itself, and traditionally referred to as an "ocular insert", vs. a device that is inserted into the eye surgically, meaning an intraocular insert placed inside the eyeball, or partly inside the eyeball itself. In fact, some devices are implanted in the layers of connective tissue forming the globe of the eyeball, and may even extend through these layers into the eyeball. And some that could be inserted topically under the eyelids could also be surgically implanted under the outermost layer, the conjunctiva, anteriorly, or Tenon's capsule, posteriorly, and would correctly be referred to as subconjunctival or sub-Tenon's inserts. This would be done via a minimally invasive procedure that does not open into the eyeball itself, but rather into the space currently utilized by ophthalmologists for sub-conjunctival or sub-Tenon's injections.

While there are conventional ocular drug delivery devices that include a drug core holding drug for release, these devices are constructed such that the drug delivery device is formed with a recess (well) that receives a separate drug core. A release membrane is then disposed over the drug core in the situation where a delayed/sustained release profile is desired. This process for forming the drug delivery device is time consuming and has certain limitations and deficiencies as discussed herein.

SUMMARY

In accordance with one embodiment, a method for forming an ocular drug delivery device includes the steps of: (1) forming a drug core containing an active agent, the drug core having a barrier disposed on all surfaces thereof except for a drug release surface which is left free of the barrier; (2) disposing an amount of a first material (e.g., first monomeric, oligomeric, resin or polymeric material) in a first mold part; (3) placing the drug core within the first mold part such that the drug release surface is in contact with the first material; (4) at least partially polymerizing the first material; (5) disposing an amount of a second material (e.g., first monomeric, oligomeric, resin or polymeric material) into the first mold part such that the second material surrounds the drug core; (6) mating a second mold part to the first mold part with the second material at least substantially filling the combined first and second mold parts; and (7) polymerizing the second material to form the ocular drug delivery device which is then removed from the first and second mold parts, the ocular drug delivery device including a drug release membrane, formed of the first material, that covers the drug release surface of the drug core and is configured to permit drug to pass therethrough over a period of time.

In accordance with the present invention, the ocular drug delivery device is produced by an overcasting process wherein the drug core is positioned in a mold and the polymerizable device body is formed by casting over the drug core to form the composite device. During this process, a thin drug releasing controlling membrane is formed in situ. The sustained release ocular drug delivery devices and methods of this invention are particularly useful in the preparation of ocular devices that contain a prostaglandin containing drug core.

In one embodiment, a sustained release ocular drug delivery device according to the present invention includes a drug core containing at least one agent effective in obtaining a diagnostic effect or effective in obtaining a desired local or systemic physiological or pharmacological effect and an impermeable layer impermeable to the passage of the active agent that surrounds at least a portion of the drug core. The drug core is disposed within the body of the drug delivery device such that the drug core is positioned adjacent to one surface of the device body. The drug delivery device has a permeable membrane (e.g., a polymeric thin layer) that is permeable to the passage of the active agent and represent a portion of one surface of the device body that is directly in contact with the drug core that provides control of drug release (drug flux). The remaining portions of the device body are formed by a polymerizable material that is cast molded (molded-over) over the drug core.

BRIEF DESCRIPTION OF THE DRAWING FIGURES

FIG. 4b is a side view of the drug core formed by the punch process of FIG. 4a;

DETAILED DESCRIPTION OF CERTAIN EMBODIMENTS

The present invention relates to a drug delivery device and more particularly, relates to a method for manufacturing a drug delivery device.

Drug Delivery Device

As mentioned previously, there are a variety of different types of ocular drug delivery devices for delivering an active agent to the eye and in general, these devices include a body that is placed in the eye and includes an active agent (e.g., a drug).

An ocular drug delivery device made in accordance with the teachings of the present invention can take the form of any of the drug delivery devices described and illustrated in applicant's own U.S. Pat. No. 8,167,855, which is hereby incorporated by reference in its entirety. The '855 patent described a number of ophthalmic drug delivery devices that each includes a body having a scleral surface having a radius of curvature that facilitates contact with a sclera of a human eye. In one embodiment disclosed in the '855 patent, the ocular device is configured for insertion into an eye and includes a body having an anterior surface and a posterior surface for placement on one of superior sclera and inferior sclera of the eye. The posterior surface is defined by a base curve that is substantially identical to a radius of curvature of the one of the superior sclera and inferior sclera of the eye. In one embodiment, the ocular device serves as an ocular drug delivery system and contains an active pharmaceutical agent, a lubricant, etc. In a second embodiment the ocular device can be constructed in such a manner to treat a wide variety of ocular conditions and diseases.

It will be appreciated that the aforementioned drug delivery device is merely one exemplary type of drug delivery device and the teachings of the present invention can be equally practiced to produce drug delivery devices having other forms as will be appreciated below.

Figure 1:
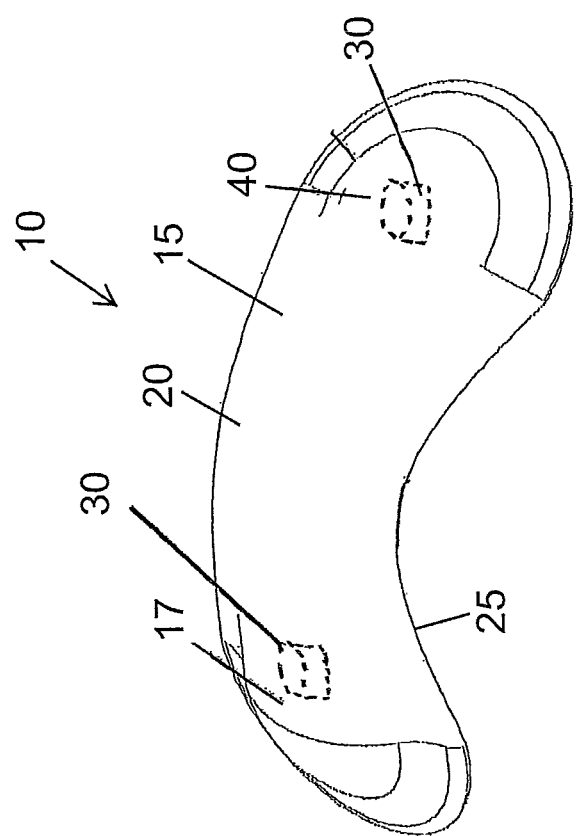
FIG. 1 is a perspective view of one exemplary ocular drug delivery device.

FIG. 1 shows an exemplary drug delivery device 10 based on the teachings of the '855 patent. The drug delivery device 10 is formed of a body 15 having an anterior surface 20 and a posterior surface 25 for placement on the sclera of the eye (e.g., on at least one of a superior sclera and inferior sclera of the eye). The posterior surface 25 has a curved shape outside of the eye prior to insertion therein and that is defined by a base curve that is complementary to and shaped to fit the sclera of the eye so as to permit the device to be held on the eye by fluid attraction and be retained on the eye without aid of an eyelid according to one embodiment. The drug delivery device 10 includes one or more structures 30 that are part of (associated with) the body 15 and contain the active agent that is to be released. For example, the structures 30 can be in the form of a drug (active agent) core (plug) that is disposed within the drug delivery device 10. As shown, the drug core 30 can be embedded within the body 15. The drug core 30 is covered by a membrane 40 that controls the release of the drug to the body and thus defines, in part, the drug kinetics of the device 10. As discussed herein, the membrane 40 is an integral part of the body 15 that overlies the drug core 30.

It will be appreciated that the drug core 30 can be located at any location of the body 15 depending upon the particular intended application so long as the drug contained therein is released and delivered efficiently to the target tissue. As a result, the membrane 40 and drug core 30 can be located along the posterior surface 25 for placement against the sclera or can be located along the opposite anterior surface 20 or even along an edge of the body 15 or drug cored can be located along both the anterior and posterior surfaces.

It will be appreciated that when a plurality of drug cores 30 are disposed within the body 15, the drug cores 30 can contain different active agents (drugs) and can have different shapes and/or sizes. For example, a larger drug core 30 can deliver a primary drug, while a smaller drug core 30 delivers a secondary drug. In addition, when a plurality of drug cores 30 are used, the drug cores 30 can be located in different areas of the body 15 in that one drug core could be located along the anterior surface 20, while the other drug core is located along the posterior surface 25. Alternatively, both can be located along the same surface.

As described in the '855 patent, the body 15 can include one or more lobes 17 which are regions of increased mass and can serve to hold the drug cores 30 as a result of such increased body mass. FIG. 1 is exemplary and shows a device 10 with two lobes 17. It will be appreciated that in FIG. 1, the drug core 30 in one lobe 17 can be located closer to the anterior surface 20 and one drug core 30 in the other lobe 17 can be located closer the posterior surface 25 to allow delivery of drug from both the anterior surface 20 and the posterior surface 25. Thus, the drug is dispensed from the anterior and posterior surfaces by positioning the drug cores 30 in different locations within the different lobes 17.

Active Agent

In accordance with the present invention, the drug core 30 contains one or more active agents. In particular, many different therapeutic agents can be delivered in the practice of this invention. Suitable active agents include, but are not limited to: antiglaucoma agents: such as adrenergics, including epinephrine and dipivefrin, epinephryl borate; beta.-adrenergic blocking agents, including levobunolol, betaxolol, metipranolol, timolol, carteolol; alpha.-adrenergic agonists, including apraclonidine, clonidine, brimonidine; parasympathomimetics, including pilocarpine, carbachol; cholinesterase inhibitors, including isoflurophate, demecarium bromide, echothiephate iodide; carbonic anhydrase inhibitors, including dichlorophenamide acetazolamide, methazolamide, dorzolamide, brinzolamide, dichlorphenamide; prostaglandins, including latanoprost, travatan, tafluprost, bimatoprost; diconosoids and combinations of the above, such as a beta-adrenergic blocking agent with a carbonic anhydrase inhibitor; Anticataract drugs: such as aldose reductase inhibitors including tolerestat, statol and sorbinil. However, other active agents can be used.

One preferred category of drugs in the practice of the present invention is the class of prostaglandins. These drugs include, but are not limited to, the commercial products latanoprost, travatan, tafluprost and bimatoprost.

Drug Core

The drug cores 30 of the present invention are generally matrices composed of a drug dissolved and/or dispersed in a matrix polymer. The polymer provides strength and allows the drug core to be fashioned in any number of geometries. The drug core 30 can have a regular shape, such as a disk (circular) or can have an irregular shape depending upon the particular application. The thickness of the drug core 30 is also selected depending upon the particular application (including in view of the amount of drug to deliver) and the drug core 30 can have a uniform thickness or in some situations, the drug core 30 can have a variable thickness in view of the selected drug kinetics and/or in view of the characteristics of the device body 15.

The drug core 30 is preferably formed of a homogenous material (homogenous mixture).

In the illustrated embodiment, the drug core 30 has a cylindrical shape since this shape is convenient to use. The matrix of the drug core 30 is produced by mixing the drug (active agent) with a monomer or pre-polymer to form a mixture that is then polymerized to form the drug core 30. As described in detail below, the drug core 30 can be formed using any number of different techniques including but not limited to a casting process or a mold process. For example, the mixture can be cast (polymerized) into a shape. The drug core 30 can be formed to have its final desired shape (i.e., by direct casting or molding) or the drug core 30 can be formed by cutting a larger structure into the final desired shape. For example, the drug core mixture can be formed (cast or mold) to have a rod or sheet structure from which the individual drug cores are produced as by cutting the rod or sheet.

Alternatively, the drug mixture can be placed is a tube constructed of a material that is impermeable to the drug and the drug cores cut from the filled tubing in the form of rings or "barrels." Examples of such tubing would be polyimide and fluoropolymers. In certain cases it may be possible to fill the tubing with the drug in neat form.

In one embodiment, the drug core 30 is constructed with the active agent being a prostaglandin for treating glaucoma. The amount of prostaglandin required per day to effectively treat glaucoma is small in the area of one microgram. Given the low daily dose required and the high cost of prostaglandins, delivery from drug core 30 is ideal. A suitable matrix for the prostaglandin is a silicone resin. Preferably, the silicone resin is platinum catalyzed and cures in the 25 to 60° C. range. One such resin, PEM-10, is available from United Chemical Technologies. Typical loadings of prostaglandin would be in the 5 to 15% range. A drug core volume of about 3 to 5 $mm^3$ is sufficient to supply at least 30 days of prostaglandin to a patient. In certain cases higher prostaglandin concentrations may be useful. Drug cores in these cases may contain prostaglandins concentrations up to about 50% or higher. When a tube is utilized to contain the prostaglandin it may be possible to utilize neat (100%) prostaglandin.

Barrier Construction

One intended drug diffusion path is from the drug core surface, adjacent to the device surface, through the thin rate controlling membrane 40 between the drug core surface and the ocular environment. It is understood that drug from the core will diffuse out of all surfaces on the core. This will lead to drug loss by diffusion into the main body 15 of the device 10. The drug in the body 15 of the device 10 is then not available to provide therapeutic value to the patient.

As a result, one will appreciate that non-productive drug diffusion must be eliminated to maximize the drug flux through the drug core surface adjacent to the ocular environment. If the drug core 30 is in the form of a cylinder then it would be necessary to place a barrier on the circular side surface and the flat bottom surface of the cylinder forming the drug core 30. This would then allow drug to diffuse only from the top surface of the drug core 30. This top surface would then be placed adjacent to the device surface to direct drug flux out of the device and into the ocular environment. In other words, the membrane 40 covers the top surface. While, the term "top surface" is used, it will be appreciated that this "top surface" through which the drug diffuses, can be oriented in a downward direction (i.e., formed along the posterior surface of the device facing the sclera in the embodiment of FIG. 1).

One technique to provide directional flux of the drug is to cast the core into a plastic container such as a barrel with an open top. There are many plastics that are excellent barriers such as polymethyl methacrylate, Teflon® and polypropylene to name a few. However, one drawback to this approach is the plastic container is that it is difficult to manufacture because of the small sizes required. Another drawback is the physical size of any plastic container that will increase the overall volume of the drug core. This approach is less desirable given the small size of the ocular device itself.

Another approach is to form the diffusion barrier around the drug core by applying a very thin film of the barrier. It is possible to apply a silica thin coating over the drug core by chemical means but this may be a costly process.

As discussed in more detail herein, one preferred method of creating a barrier on the drug core 30 is the application of a parylene barrier thin film. parylene is the trade name for a variety of chemical vapor deposited poly (p-xylylene) polymers used as moisture and dielectric barriers. Among them, parylene C, is the most popular due to its combination of barrier properties, cost, and other processing advantages. Parylene is self-initiated (no initiator needed) and un-terminated (no termination group needed) with no solvent or catalyst required. Polymerization occurs at a very low pressure and at near room temperature. The entire process is known as CVD, or Chemical Vapor Deposition. The resulting parylene film which has bonded during the deposition process and becomes a thin, microns in thickness, protective coating. Unlike liquid coatings, parylene completely penetrates all crevices and uniformly coats surfaces such as sharp points, cavities, edges, corners and even the minutest pores. It conforms to almost any exposed surface and is pinhole free. Parylene provides unsurpassed barrier protection against organic as well as inorganic compounds.

Other methods of creating a barrier coating can be utilized such as plasma treatment, plasma polymerization and metal vacuum deposition.

Integral Release Membrane

The integral drug release controlling membrane can be formed in situ as a step in the overcast process disclosed in the present invention. The release membrane is first chosen to provide the desired drug release rate or flux. The membrane itself is a polymeric material and can be formed from monomer(s), oligomers, resins or a polymer. The material forming the release membrane must be of sufficient viscosity to adhere the drug core to the surface of the casting mold. A viscosity of about 5000 cps to about 1,000,000 cps will provide the adhesion necessary to secure the drug core to the mold surface while forming a thin film between the core and the mold surface. This film will form a release membrane approximately about 100 microns to about 1000 microns thick. In the case of monomer or monomers it is generally necessary to partially polymerize them on the surface of the mold to achieve the proper viscosity for adhering the drug core to the mold surface. Monomer(s) such as acrylics and styrenics are examples of such systems. Oligomer and resin systems such as silicones, urethanes and epoxies may be viscous enough not to require partial polymerization to provide the drug core adherence. Polymers such as acrylics and sytrenics may be useful in forming release membranes. In these cases the polymer would be dissolved in a suitable solvent to obtain a viscous solution. This solution would be applied to the mold surface and the drug core adhered to the mold. The solvent would then be allowed to partially or fully evaporate before the over cast with the matrix system. It should be noted that many monomer/polymer systems can be utilized to form the integral drug release rate controlling membrane.

Ocular Device Body—Material

The ocular device body 15 is polymeric in nature and is constructed by casting monomers, oligomers or resins in molds or the like. The polymerization process can be carried out at low temperatures preferably in the 25 to 80° C. range. When the device body 15 is prepared from ethylenically unsaturated monomers it is preferable to employ a UV initiator and UV polymerization process. The acrylic and methacrylic families of monomers are preferred to construct the device body. Alternatively, silicone materials can be used to cast the device body. Silicones have several advantages in that many are classified as medical grade, they are readily available, they are easily cast, they can cure at room temperature and are biocompatible. For the practice of this invention, is preferable to employ platinum catalyzed silicones since no byproducts are generated during the curing process. Two silicones are particularly useful to prepare the device body, namely, Dow Corning Silastic® MDX4-4210 a polydimethyl siloxane and Nusil MED 50-5338 a fluorosilicone.

Other materials can be utilized to cast the device body such as polyurethanes, epoxies and styrenic monomers can also be utilized. Applicant's own published application No. 2010-0178315, which is hereby incorporated by reference in its entirety.

Method of Making Ocular Drug Delivery Device

Figure 2:
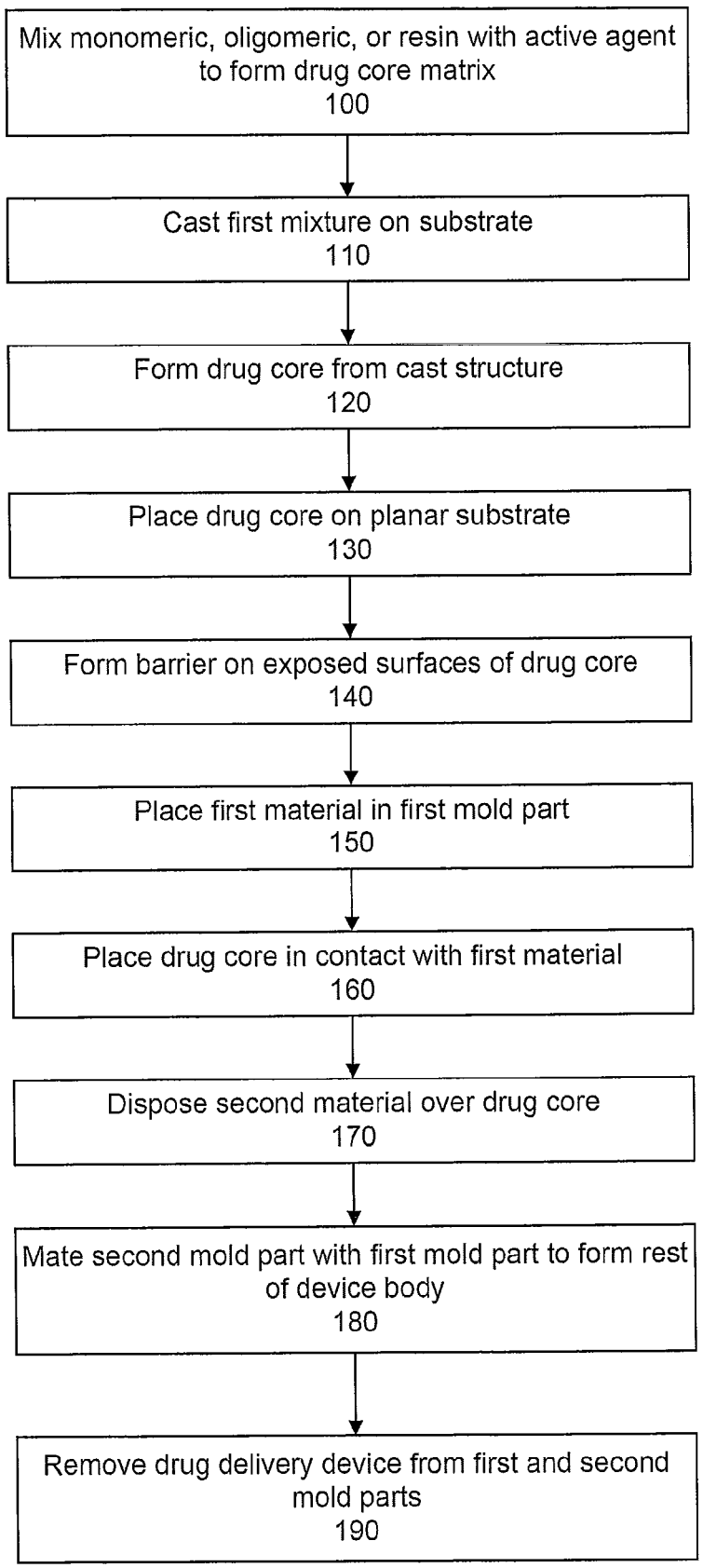
FIG. 2 is a schematic showing the steps of one exemplary method for forming the ocular drug delivery device of FIG. 1.

In accordance with the present invention, a method of manufacturing an ocular delivery device (e.g., ocular drug device 10) is set forth in the flow chart of FIG. 2. In a broad sense, the present invention involves the formation of a drug core which is then incorporated into the body of the drug delivery device with a release membrane being formed in situ adjacent to the drug core. FIG. 2 shows the steps of one exemplary method and includes a first step 100 in which a material (e.g., a monomer, oligomer, resin or polymer) is mixed with an active agent to form a first mixture. The first mixture is thus polymerized to form the active agent dissolved/dispersed in a polymerized matrix.

The active agent and polymer used to form the first mixture can be selected from any one of the materials mentioned hereinbefore with reference to FIG. 1 and the other figures of the present invention. In one embodiment, the polymer is a silicone resin and the active agent is a prostaglandin.

The polymer and active agent are mixed using conventional equipment and according to conventional techniques to form, in one embodiment, a homogenous mixture. The active agent is preferably substantially (uniformly) dispersed throughout the matrix.

After the first mixture is prepared, the drug core 30 (FIG. 1) is formed. While the core 30 is described as being a drug core, it will be appreciated that the active agent contained therein does not have to be per se a drug but can be another therapeutic agent.

Figure 3:
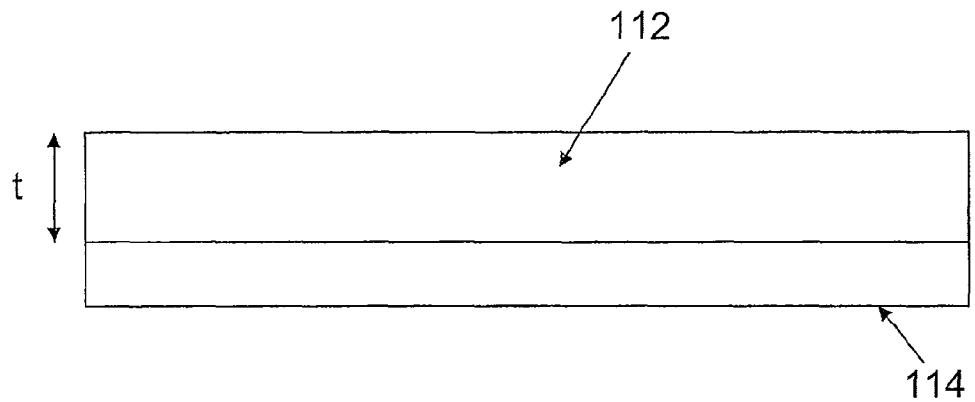
FIG. 3 is a side view of one exemplary cast structure formed of a polymeric matrix including an active agent.

As mentioned herein, the drug core 30 can be formed using any number of different techniques including but not limited to a casting process and a mold process. FIG. 2 shows one method of forming the drug core and includes a second step 110 of casting the first mixture (to form a cast structure 112) on a substrate 114 to a predetermined thickness (t). In this embodiment, the cast structure can be a film or block structure (preferably formed of a homogenous material). In one embodiment, the thickness (t) of the cast structure 112 is about 1 mm. FIG. 3 shows such arrangement.

Figure 4A:
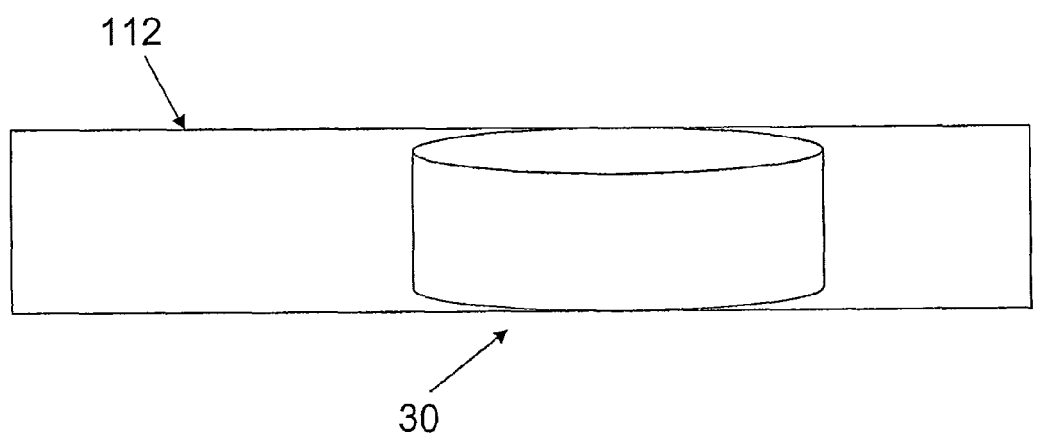
FIG. 4a is a side view showing a drug core being punched from the cast structure of FIG. 3.
Figure 4B:
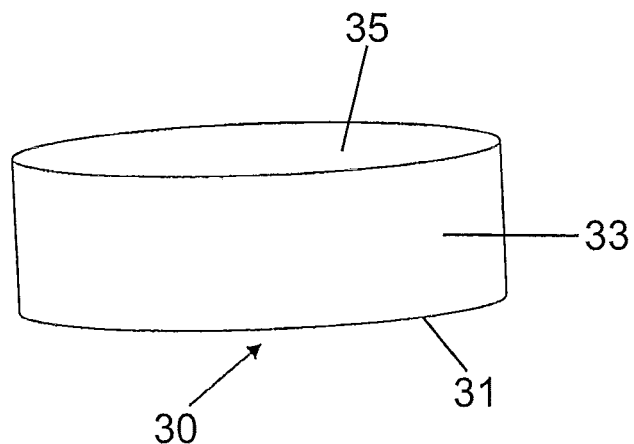

In step 120, the drug core 30 is formed from the cast structure 112 as by cutting the drug core 30 from the cast structure 112 such that the drug core 30 has the desired predetermined shape (e.g., a cylinder). In other words, a punch process can be used to form the drug core 30 from the cast structure 112. FIGS. 4a and 4b show the punch process to form drug core 30 (FIG. 4b) having the intended shape (e.g., cylindrical shape).

It will be appreciated that when a direct cast or direct mold process is used, the step 120 can be eliminated since the drug core 30 is formed having its final intended shape and thus a punch process is not needed.

Figure 5:
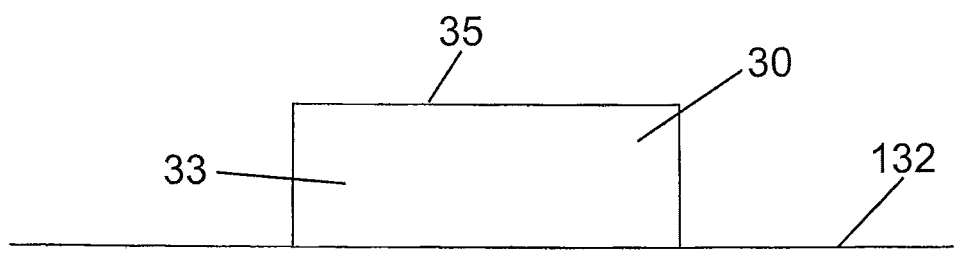
FIG. 5 is a side view showing the drug core placed on a planar surface.

In step 130 and as shown in FIG. 5, the drug core 30 is placed on a planar surface (substrate) 132. One face 31 of the drug core 30 is thus in direct contact with the planar surface 132. The remaining faces (such as side face 33 and face 35) are exposed.

In step 140, a barrier 145 is disposed on the exposed surfaces of the drug core 30 that is resting on the planar surface 132. As mentioned herein, the barrier 145 can be in the form of a film that is deposited on the exposed surfaces (faces) of the drug core 30. In the embodiment shown in FIG. 5, the barrier 145 is deposited on the side face 33 and face 35, with face 31 not being coated with the barrier 145.

Figure 6:
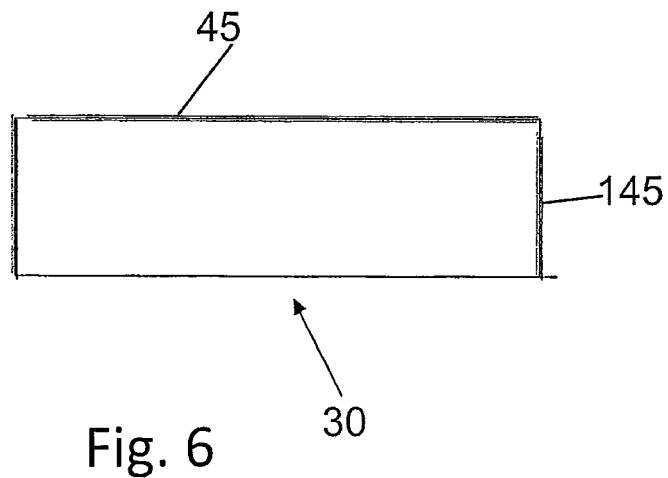
FIG. 6 is a side view showing a barrier (film) being deposited on exposed surfaces of the drug core.

The result of the step 140 is shown in FIG. 6 and in particular, the one face 31 remains an uncoated surface that is free of the barrier 145. It will be appreciated that the one face 31 represents the face of the drug core 30 through which the drug diffuses (as a result on being free of the barrier 145).

As described herein, the present invention utilizes an overcastting (overmold) process for manufacturing the release membrane and the body of the device.

Figure 7:
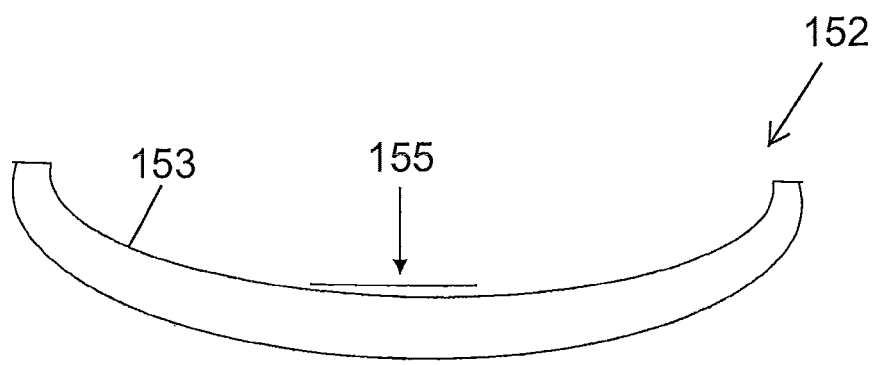
FIG. 7 is a side view of a first material (e.g., first monomeric, oligomeric, resin or polymeric material) being disposed in a select location of one face of a first mold part.

In step 150, a first mold 152 is provided and includes a surface 153 that receives a moldable material (first material in the form of a monomeric, oligomeric, resin or polymeric material) that forms body 15. The first mold 152 can be in the form of a first (bottom) casting cup that is constructed to form part of the ocular device of the present invention (e.g., device 10). In one embodiment, the first mold 152 is in the form of a polypropylene bottom casting cup mold and the surface 153 represents a concave surface thereof. In step 150, a predetermined amount of a first material (e.g., a first monomeric, oligomeric, resin or polymeric material) 155 is deposited on a select area of the first mold 152 (i.e., on a select target location of the surface 153). The select target location on which the first material is deposited is selected in view of the final location of the drug core 30 with respect to the body 15. In particular, the first material 155 is deposited in an area of the first mold 152 in which the drug core 30 is to be placed and located. In the illustrated embodiment, the first material 155 is deposited in a central (middle) location of the surface 153; however, this location is merely exemplary in nature. This is shown in FIG. 7.

The first material 155 can be the same material or a different material relative to the material that is used to form the drug core 30. In one embodiment, the first material 155 is a silicone (resin) material.

Figure 8:
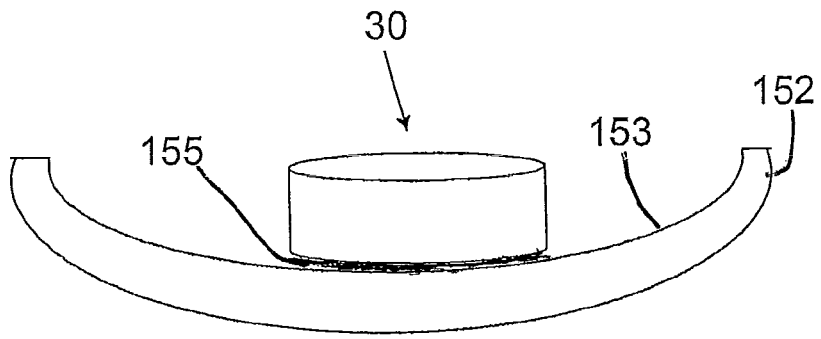
FIG. 8 is a side view of a barrier (layer) being formed on exposed surfaces of the drug core with an uncovered face of the drug core contacting the first material.

In FIG. 8 and according to step 160, the formed drug core 30 with barrier 45 covering one or more faces thereof is disposed on the surface 153 such that the uncovered face 31 contacts the first material 155. The drug core 30 can be pressed against the surface 153 with the first material 155 being disposed therebetween. The first material 155 thus forms the release membrane that is formed adjacent the face 31 and is constructed to allow the drug to diffuse therethrough.

The first material 155 can thus be thought of as, in one embodiment, being a polymerizable material.

In one embodiment, the first material 155, in the case of a monomeric, oligomeric, resin or polymeric material, is allowed to at least partially cure (e.g., turn tacky to the touch) or in the case of a polymer solution is allowed to dry so as to ensure that the drug core 30 remains in the desired target location when the drug core 30 is disposed on the first material 155. However, it is within the scope of the present invention that the drug core 30 can be disposed on the first material 155 prior to the partial cure thereof. The combined core and first material are then allowed to sit for a predetermined period of time to allow partial curing of the first material.

The cure time for the first material (e.g., first monomeric, oligomeric or resin material) 155 varies depending upon the type of first material used; however, in most embodiments, the partial cure time can be a few hours or less (e.g., 2 hours or less; 1 hour or less, etc.). The first material 155 (e.g., first monomeric, oligomeric, or resin material or can be a polymeric material) can be fully polymerized at a later time.

Figure 9:
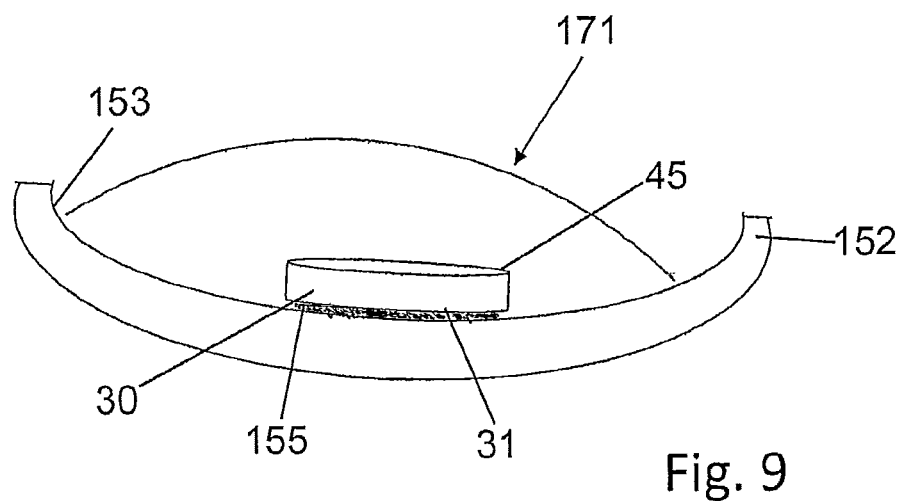
FIG. 9 is a side view showing a second material (e.g., first monomeric, oligomeric, resin or polymeric material) disposed over the structure that is disposed within the first mold part and more particularly, the second material is disposed over the drug core and barrier.

In FIG. 9 and according to step 170, a second material 171 (e.g., a monomeric, oligomeric, resin material) is disposed over the structure that is disposed within the first mold 152 and more particularly, the second material 171 is disposed over the drug core 30 that rests on and is coupled to (via a bond) the first material 155. The second material 171 thus covers the barrier layer 45 of the drug core 30 and spreads throughout the first mold 152 to form the intended shape of the ocular drug delivery device (e.g., device 10) (volume of second material can be greater than volume of mold cavity so as to at least fill the cavity).

The second material 171 can be the same material as the first material 155 or it can be a different material. Similarly, the second material 171 can be the same material or a different material relative to the material used to form the first mixture. The first and second materials can thus be curable/polymerizable materials that are suitable for use in the intended environment as an ocular drug delivery device.

The step 170 can be thought of as being an overcasting or overmolding process that forms the body 15 of the device 10 around the drug core 30 (that includes barrier 45) and the material is thus one that can be cast and polymerized.

Figure 10:
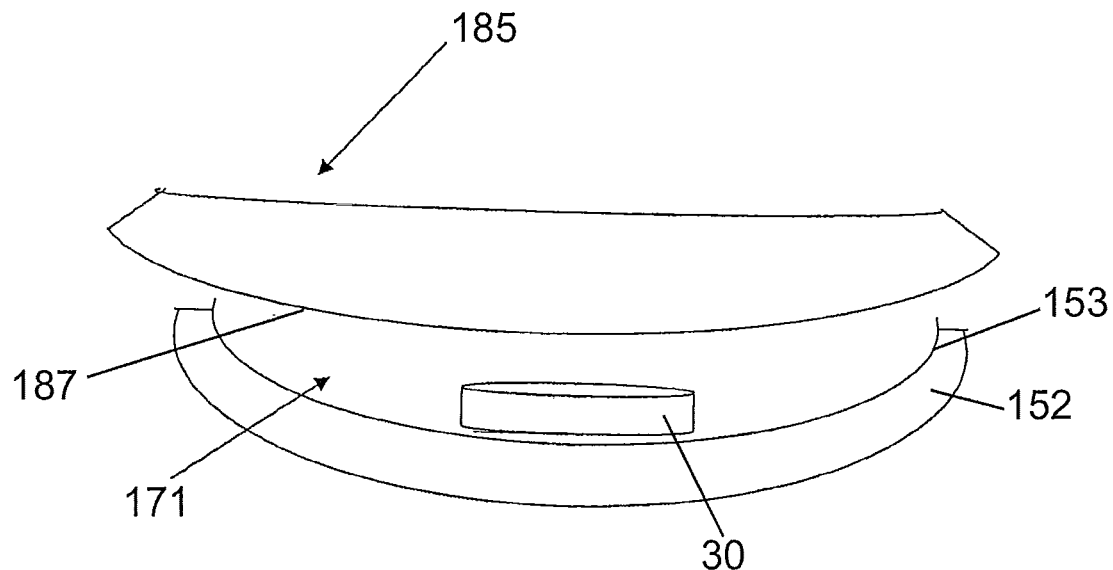
FIG. 10 is a side view showing a second mold part mating with the first mold part to form a complete mold shaped to form the final ocular drug delivery device.

In FIG. 10 and according to step 180, a second mold 185 is mated with the first mold 152 with the second material 171 spreading throughout the mated molds 185, 152. The second mold 185 can be in the form of a second (top) casting cup that is constructed to form the other part of the ocular device of the present invention (e.g., device 10). In one embodiment, the second mold 185 is in the form of a polypropylene top casting cup mold having a surface 187 that faces the surface 153 of the first mold 152. Excess second material will then be discharged from the mold when the two molds are mated together (in overcastting, excess second material is usually added).

It will be understood that step 180 can be completed prior to step 170 in that the two molds 152, 185 can be mated together to define a mold cavity that surrounds the drug core and the second material is then delivered into the mold cavity. The second material flows around the drug core and the first material that is within the combined mold. The second material is then polymerized to form the device body around the drug core.

The materials (including the second material 171 in the form of a monomeric, oligomeric or resin material) can then be fully polymerized to form the complete final ocular drug delivery device (e.g., device 10). After the ocular drug delivery device is formed, the mold parts 152, 185 are separated and the drug delivery device is removed in step 190.

It will be appreciated that that instead of first adding an amount of a second material to the first mold part, the first and second mold parts can be mated to one another to form and define an interior mold cavity and the second material is then delivered (e.g., injected) into the interior mold cavity.

Figure 11:
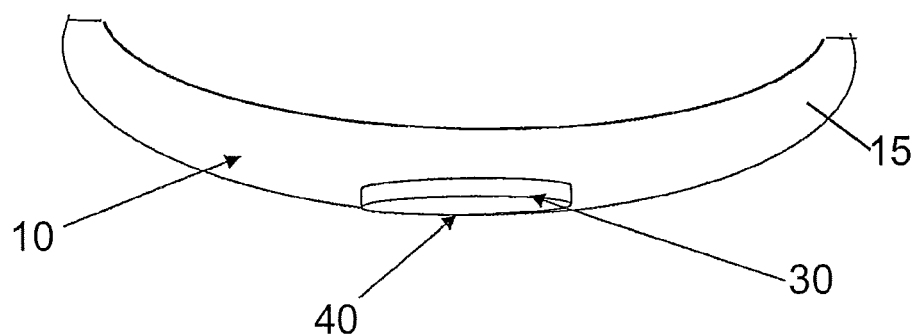
FIG. 11 is a side view of one exemplary drug delivery device.

FIG. 11 shows one exemplary drug delivery device 11 that is similar to device 10 of FIG. 1 and includes and is formed of body 15, embedded drug core 30, release controlling membrane 40 that covers the face of the drug core 30 that is free of the barrier 45.

In accordance with the present invention, the resulting ocular drug delivery device contains an embedded drug core 30 adjacent to one surface of the device separated from the ocular environment by the thin release controlling membrane 40 that was formed in situ during the manufacturing process.

The manufacturing process for producing the drug delivery devices of this invention is thus cast molding. In this process a monomer(s), oligomer or resins are placed in a plastic casting mold bearing the geometry of the ocular device. Thermal exposure, UV or visible light exposure or a combination of both polymerizes the monomer(s), oligomer or resin. The device is then removed from the mold. Post processing may be required, for example edge finishing. In the case of an ocular device polypropylene casting molds are preferred. Most preferred is a polypropylene resin with a melt flow index above 20. One polypropylene resin is Exxon PP1105E, which has a melt flow index of 34 g/10 min. With melt flows above 20 gm/10 min intricately shaped casting molds can be injection molded with excellent replication of part dimensions using modern CAD/CAM technology and engineering. Other resins such as polystyrene, polyester, polymethylpentene, polyolefins to name a few are also useful to produce casting molds.

It will be understood that the overcasting (overmolding) process is basically a casting operation that utilizes a two part mold with the distinction that one mold half contains a positioned insert (i.e., the drug core 30) that is cast over and becomes embedded in the final product (drug delivery device 10).

The present invention utilizes an over casting process to produce an ocular drug delivery device 10 in which the drug core 30 is embedded in the device 10 adjacent to one surface of the device 10.

The method of the present invention offers a number of advantages compared to conventional techniques for forming a drug core in a device and more particularly, the method of the present invention is characterized as containing the following advantages: (1) the process is less complex than the previous techniques; (2) the process is applicable to low cost manufacturing; (3) the process is amenable to placing a drug core(s) in essentially any position on the drug delivery device; (4) the process is amenable to placing more than one drug core in one device; (5) the process is amenable to placing different drug core compositions in one device; (6) the process is amenable to utilizing different drugs in different cores placed in one device; (7) the process is amenable to provide a combination drug delivery device; (8) the process is amenable to placing one core(s) on the anterior device surface and one core(s) on the posterior device surface; and (9) the method allows for flexibility in design and manufacture since there is flexibility in that the drug(s) selection and concentration; the core(s) polymeric material; barrier coating; release membrane; and device matrix material can be varied independently.

As explained with reference to FIG. 1, the drug core 30 in one lobe 17 can be located closer to the anterior surface 20 and one drug core 30 in the other lobe 17 can be located closer the posterior surface 25 to allow delivery of drug from both the anterior surface 20 and the posterior surface 25. Thus, the drug release membrane 40 is dispensed from the anterior and posterior surfaces by positioning the drug cores 30 in different locations within the different lobes 17. In this type of construction, the first mold part 152 has a drug core 30 and release membrane 40 associated therewith and the second mold part 185 has a drug core 30 and release membrane 40 associated therewith. When the overmold (overcast) material (second material) is added between the two mold parts, the material flows around the two drug cores and membranes associated with the two different mold parts that oppose one another. The remaining body of the device is thus formed in this manner. Thus, the present invention can include two separate mold parts that have previously prepared drug cores coupled thereto (e.g., as by fully polymerizing the membrane 40 adjacent to the drug core 30) prior to mating of the mold parts and injection of the material that forms the rest of the body of the drug delivery device.

It will thus be understood that in the present method, the drug core is initially positioned within the mold and the drug release membrane is at least partially formed in the mold before subsequently, performing an overcast process in which a polymerizable material is added to a mold cavity between two mold parts. The polymerizable material flows around the drug core and the drug release membrane and there can be bonding between the polymerizable material and the drug release membrane such that when the polymerizable material is polymerized, an integral drug delivery device body is formed. The device body is thus formed around the drug core(s).

While the present method has been described in some embodiments as using a polymerization process as part of the overmold (overcast) process to form the final body of the drug delivery device, it will be appreciated that the body of the device can be formed by other techniques so long as it is part of an overcast process in which the body is formed around the already formed drug core which is located within the mold.

EXAMPLES

The following examples illustrate certain aspects of certain exemplary embodiments described herein. It will be understood that the following examples are thus merely exemplary in nature and not limiting of the scope of the present invention.

Example 1

This example describes an ocular device 200 for insertion into an eye is provided and includes a body having an anterior surface 210 and a posterior surface 220 for placement on one of superior sclera and inferior sclera of the eye. The posterior surface 220 is defined by a base curve that is substantially identical to a radius of curvature of the one of the superior sclera and inferior sclera of the eye.

Casting molds conforming to the above description were generated by injection molding of a high melt flow polypropylene. The casting mold consisted of a bottom cup and a fitted top cover that form a tightly sealed unit when assembled. For the purposes of this example the casting mold design was that of a topical ocular device but by no means limited to any one specific design.

Figure 12A:
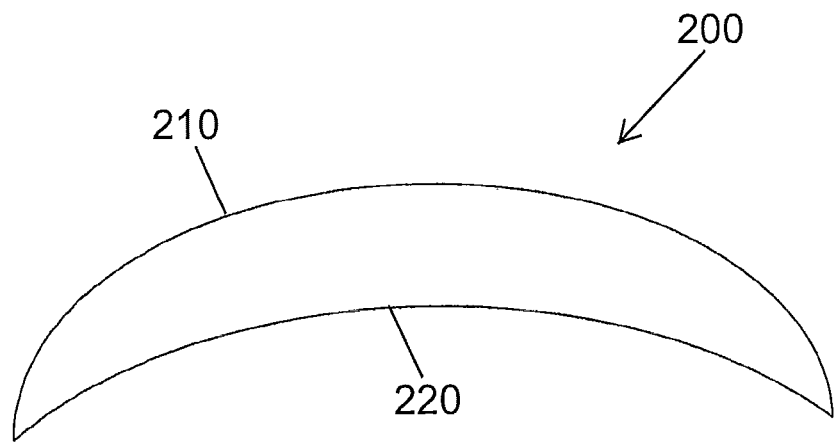
FIG. 12A is a side view of another exemplary ocular drug delivery device formed in accordance with the process of the present invention.
Figure 12B:
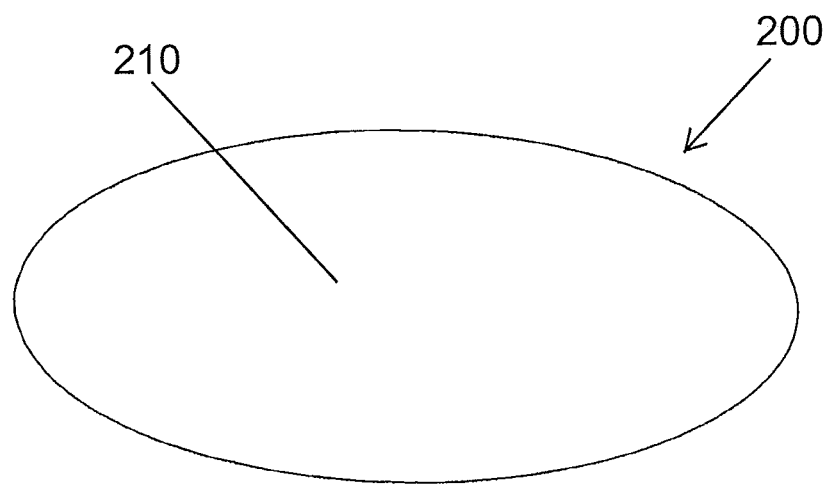
FIG. 12B is a top plan view of the ocular drug delivery device of FIG. 12A.

The device produced in accordance with this example is shown in FIGS. 12A and 12B.

Example 2

In this example, the active agent that is used in the drug core of the ocular drug delivery device made in accordance with the present invention is a prostaglandin. Prostaglandins are available from Cayman Chemical in neat form. The prostaglandin utilized in the patent examples is latanoprost purchased from Cayman Chemical.

Latanoprost: Cayman Chemical Item Number 10011176 (CAS130209-82-4)

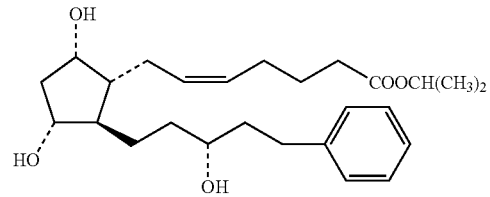

Example 3

In this example, the drug delivery device is formed using the following silicone resin as a matrix for prostaglandin (the active agent): Supplier: UCT Specialties, LLC; Product: PEM10; Description: Two Part RTV Silicone Elastomer Kit, 10 Parts A; 1 Part B; Components: A silicone hydride prepolymer and a vinyl silicone prepolymer with a platinum catalyst; and Properties: Non filled, Low viscosity, fast low temperature cure

Example 4

This example describes the incorporation of a prostaglandin, Latanoprost, into a silicone material. The following formulation was prepared: (10% Latanoprost); PEM-10 Part A: 0.49 gms, PEM-10 Part B: 0.05 gms; Latanoprost: 0.06 gms.

Preparation

Weigh out the formulation and mix by hand for about 10 minutes along with scrapping the sides and bottom of mixing container with a spatula to eliminate "dead' spots. Place formulation in a bell jar and apply full vacuum for about 5 minutes to remove air bubbles. The resulting de-gassed formulation was hazy.

Casting

After de-gassing the formulation was poured into an aluminum dish to a depth of about 1 mm. The dish was then placed in a 37° C. hot air oven and allowed over 24 hours to complete the polymerization. The resultant Latanoprost/silicone thin sheet was removed from the dish.

Example 5

The Latanoprost/silicone thin sheet of Example 4 was utilized to prepare small drug core samples. Using a General Tools and Instruments Awl #72 (with a 2.0 mm diameter punch) small drug cores were punched out from the thin sheet. These cores were cylindrical with dimensions of about 2.0 mm diameter by about 1.0 mm height and weigh about 3+ mg.

Example 6

This example describes the application of a barrier coating to the Latanoprost/silicone drug cores described in Example 5. A convenient size of polyethylene sheet was cut out and coated with a thin film of tacky silicone. The drug cores were adhered to the polyethylene via the tacky silicone film and spaced apart by a few millimeters. The samples were coated with the barrier polymer "Parylene" on the cylindrical surface and the exposed top of the drug cores. The Parylene acts as a barrier to prevent the Latanoprost from releasing from the coated surfaces. The only non-coated portion of the drug core is the flat surface adhered to the silicone/polyethylene sheet. After coating the drug cores were removed from the polyethylene sheet.

Example 7

Figure 13:
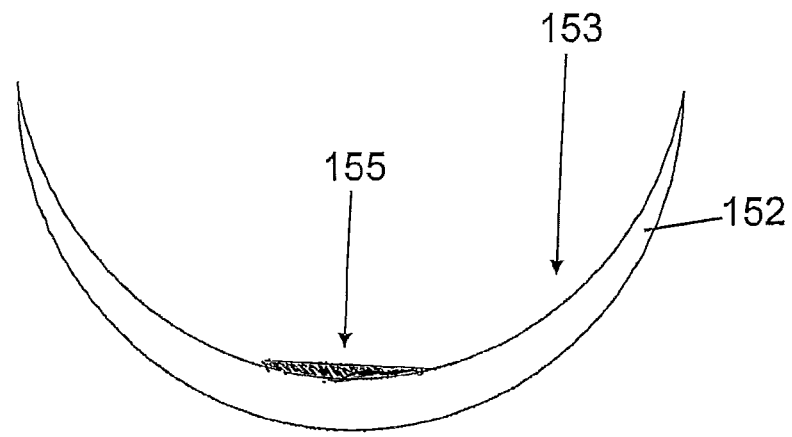
FIG. 13 is a side view of a first mold part showing an anterior mold surface with first material deposited thereon.
Figure 14:
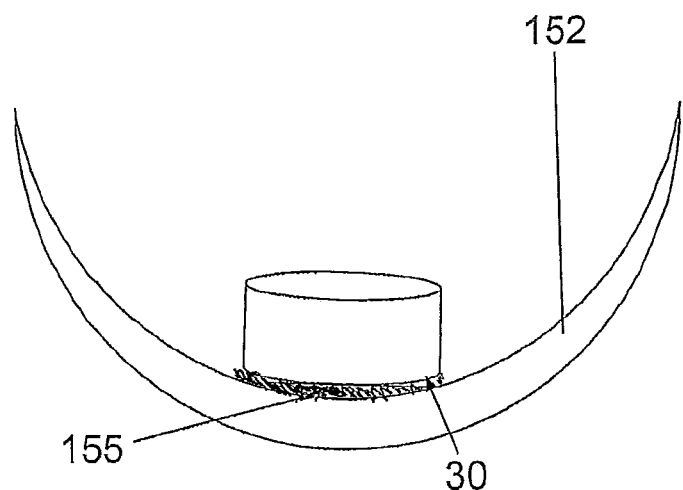
FIG. 14 is a side view of the first mold part of FIG. 13 showing a drug core disposed on the first polymeric material.

This example details the placement of the drug containing silicone drug core on the polypropylene anterior surface mold half and is shown in FIGS. 13 and 14. A small quantity of Dow Corning silicone MDX4-4210 was prepared according to the labeled instructions. A small amount of the mixed silicone resin 155 was placed at the bottom 153 of the polypropylene anterior mold half 152. A drug containing silicone core 30 from Example 6 was then centrally positioned by pressing the non Parylene coated flat surface into the silicone resin in the mold (schematic below). This creates a thin silicone film between the drug core and the mold surface. The mold assembly was then placed in a 37° C. hot air oven for about 2 hours to partially cure the silicone resin and secure the drug containing silicone drug core to the mold half. The mold assembly is now ready for the overcasting process.

Example 8

Figure 15:
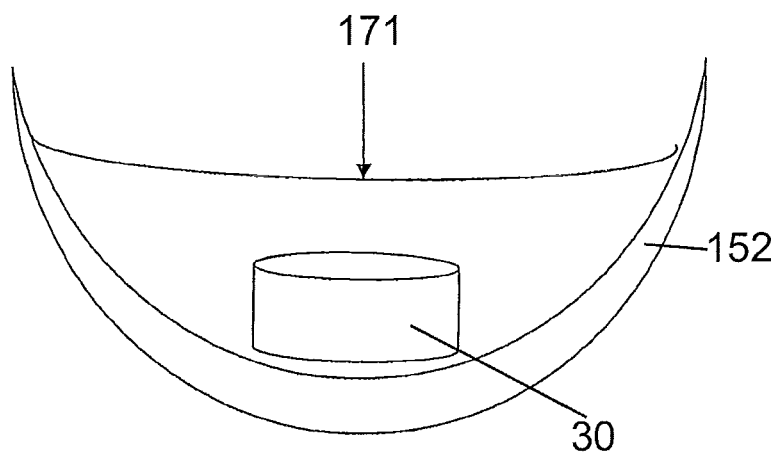
FIG. 15 is a side view of the first mold part of FIG. 13 showing the second material deposited over the drug core.
Figure 16:
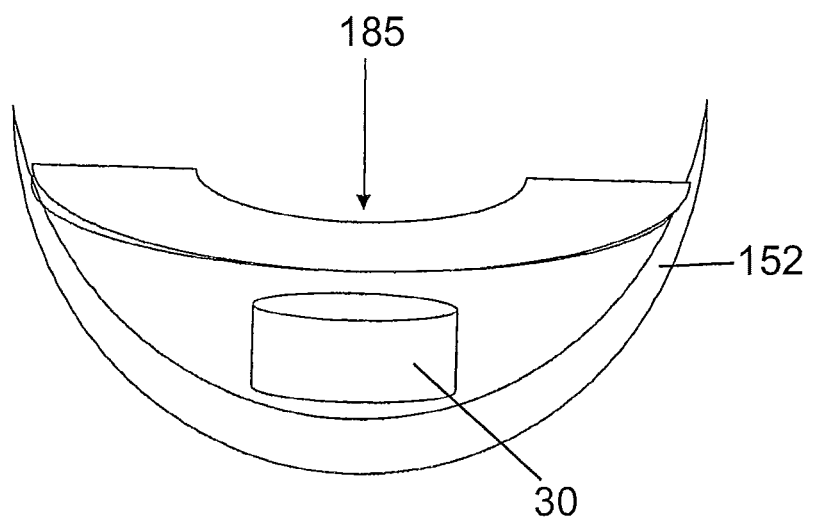
FIG. 16 is a side view of a second mold part mated with the first mold part.
Figure 17:
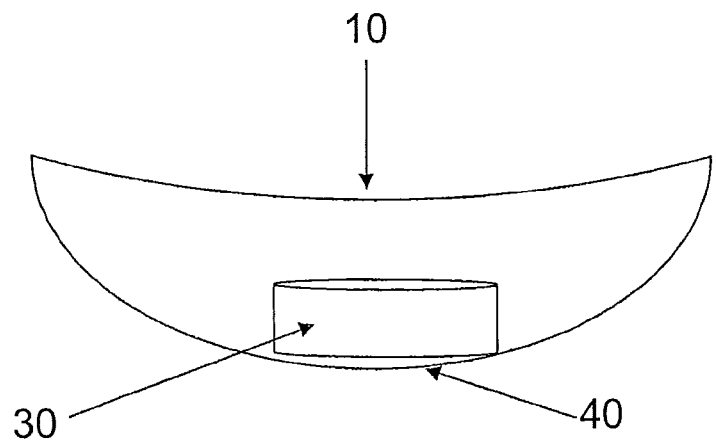
FIG. 17 is a side view of a resulting drug delivery device.

This Example, with reference to FIGS. 15 and 16, describes the manufacture of a drug delivery device utilizing the mold assembly from Example 7. The body of the drug delivery device comprises a Dow Corning silicone MDX4-4210 medical grade silicone resin. The silicone resin 171 was prepared according to the labeled instructions. A quantity of the resin 171 was placed in the mold assembly 152 (schematic below) encapsulating the drug containing silicone drug core 30. The top polypropylene mold half 185 was then placed over the bottom polypropylene mold bottom and pressure was applied by clamping to mate the two mold halves and create the device geometry. The clamped mold assembly was placed in a hot air oven at 37° C. for about 2 days to cure the silicone resin. After the curing process was complete the finished device was removed from the mold and is shown in FIG. 17. The device 10 was roughly circular with a diameter of about 10 mm and weighs approximately 50 mg. When placed in the eye the drug will be released from the anterior surface of the device, through the thin silicone release membrane 40, into the ocular environment.

Example 9

Figure 18:
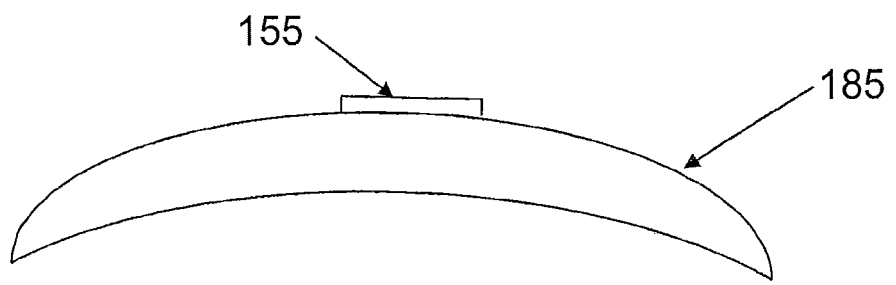
FIG. 18 is a side view of a mold part including a posterior mold surface with a first material disposed on the posterior mold surface.
Figure 19:
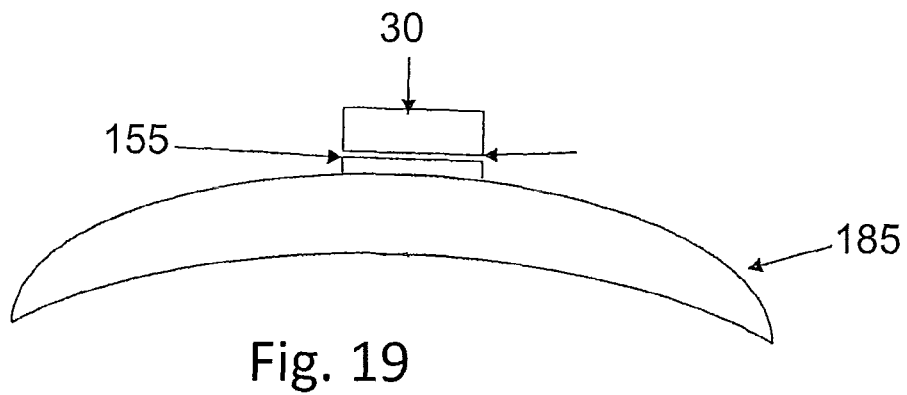
FIG. 19 is a side view showing a drug core disposed on the first polymeric material of FIG. 18.

With reference to FIGS. 18 and 19, this example details the placement of the drug containing silicone drug core on the polypropylene posterior surface mold half 185. A small quantity of Dow Corning silicone MDX4-4210 was prepared according to the labeled instructions. A small amount of the mixed silicone resin 155 was placed centrally at the top of the polypropylene posterior mold half 185. A drug containing silicone core 30 from Example 6 was then positioned by pressing the non Parylene coated flat surface into the silicone resin in the mold. This creates a thin silicone film between the drug core 30 and the mold surface. The mold assembly was then placed in a 37° C. hot air oven for about 2 hours to partially cure the silicone resin and secure the drug containing silicone drug core to the mold half. The mold assembly is now ready for the overcasting process.

Example 10

Figure 20:
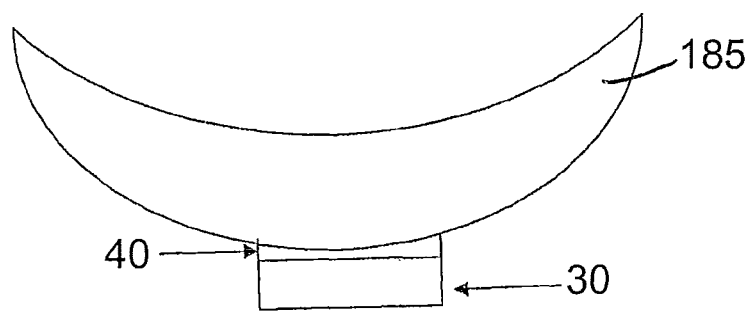
FIG. 20 is an exploded side view showing the mold part of FIG. 19 serving as a top mold part that is mated with a bottom mold part that contains a polymerizable material.
Figure 21:
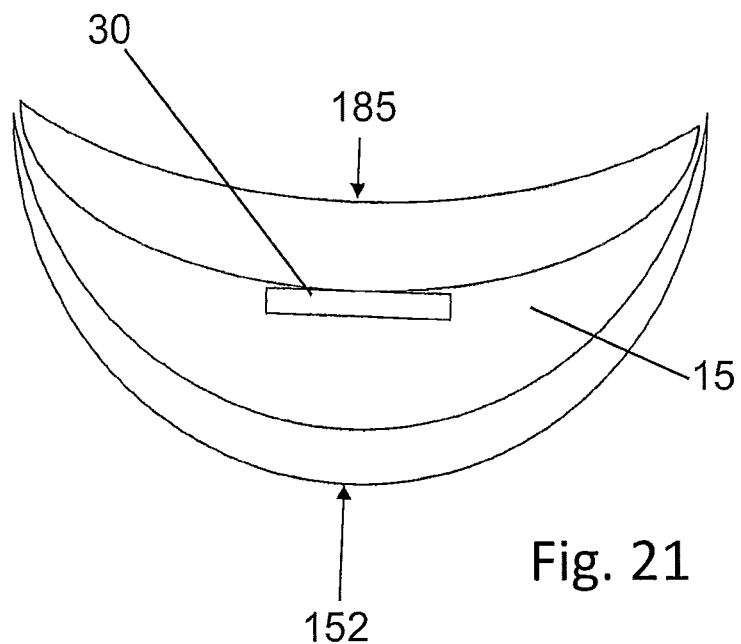
FIG. 21 is a side view showing the top and bottom mold parts of FIG. 20 mated together.
Figure 22:
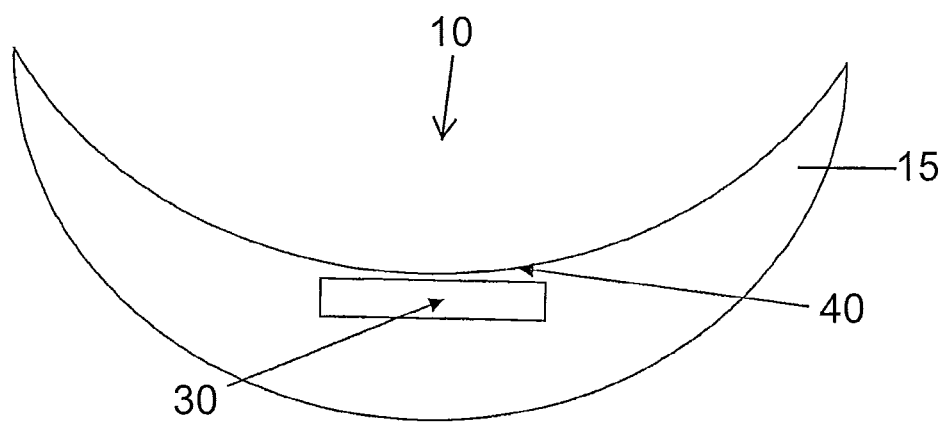
FIG. 22 is a side view of the resulting drug delivery device from the mold parts of FIG. 21.

With reference to FIGS. 20-22, this Example describes the manufacture of a drug delivery device utilizing the mold assembly from Example 9. The body of the drug delivery device comprises a Dow Corning silicone MDX4-4210 medical grade silicone resin. The silicone resin was prepared according to the labeled instructions. A quantity of the resin was placed in the mold assembly 152. The top polypropylene mold half 185 containing the silicone drug core 30 was then placed over the bottom polypropylene mold bottom and pressure was applied by clamping to mate the two mold halves and create the device geometry. The clamped mold assembly was placed in a hot air oven at 37° C. for about 2 days to cure the silicone resin. After the curing process was complete the finished device 10 was removed from the mold. The device was roughly circular with a diameter of about 10 mm and weighs approximately 50 mg. When placed in the eye the drug will be released from the posterior surface of the device, through the thin silicone release membrane, into the ocular environment.

Example 11

This example describes an acrylic formulation for the construction of a drug delivery device wherein the device body comprises an elastomeric, non-hydrating. acrylic material.
Formulation Ingredients
DEGEMA Di(ethylene glycol) ethyl ether methacrylate
TFEM Trifluoroethyl methacrylate
TFEA Trifluoroethyl acrylate
PEGDM Poly(ethylene glycol) dimethacrylate
MA Methacrylic acid
KIP 100F Monomeric and oligomeric alpha hydroxyl ketone
Acrylic formulation Proportions in Volume/Weight

| | |
|---|---|
| DEGEMA | 65.0 ml |
| TFEM | 25.0 ml |
| TFEA | 5.0 ml |
| PEGDM | 5.0 ml |
| MA | 1.0 ml |
| KIP 100F | 0.40 g |

All Weights/Volumes are +/−0.5%
Base Formulation Preparation
1. Use purified monomers only. The initiator is used as is; 2. To glass sample vial of appropriate size, add the weighed initiator; 3. Pipette the monomers into the vial, cap, and begin stirring with the aid of a magnetic stir bar; 4. Stir for 10 minutes to ensure proper mixing of all components; and 5. Process the formulation same day as prepared or store mixed formulation in the refrigerator (about 40° F.) for up to thirty (30) days before use.

Example 12

This Example describes the construction of a drug delivery device with a silicone drug core overcast with an acrylic formulation to produce a device that releases drug from the anterior surface. Firstly, the assembly described in Example 7 is produced. Secondly, the polypropylene mold half is filled with the acrylic formulation of Example 11 and the top mold half is mated with the bottom mold half as described in Example 8 except that the polymerization cycle is carried out by UV exposure as detailed here. The clamped mold is placed in a 365 nm UV oven and the exposure time set to 30 minutes. The dose rate is about 277,777 micro joules per $cm^2$ per minute. The total dosage received in 30 minutes is about 8.33 joules per $cm^2$. After polymerization the device is removed from the mold. The acrylic body was clear and elastomeric. The drug containing core was encapsulated in the acrylic body with its thin silicone release controlling membrane.

Example 13

The drug release from the overcast drug delivery devices were carried out using a phosphate buffer system containing polysorbate 80. This buffer is described here.
The drug release buffer solution is composed of:
Product Name: Phosphate buffer solution in $H_2O$
Product Number: 319252 (Sigma)
Product Brand: FLUKA
the pH and osmolarity are: pH=7.22 and Osm=108;
and Polysorbate 80(HX)™ from NOF Japan.
The Polysorbate 80 concentration is 0.1% in the Phosphate Buffer Solution (PBS)

Example 14

The devices of Examples 8, 10 and 12 were subjected to in vitro Latanoprost release studies utilizing the buffer described in Example 13.

The release methodology presented here utilizes both a 37° C. water bath and a 37° C. hot air oven to carry out the release experiments. The description of release testing methodology is as follows:
Release #1—1st day; sample in 10 ml of buffer for 1 day
Release #2—2nd day; sample in 100 ml of buffer for 1 day
Release #3—3nd day; sample in 10 ml of buffer for 1 day
Release #4—Sample placed in 100 ml of buffer for 2 days
Release #5—Sample placed in 10 ml of buffer for 1 day
Release #6—Sample placed in 100 ml of buffer for 3 days
Then repeat the same cycle as Release #5 and Release #6 for at least 30 days.

Only the 10 ml samples are analyzed for drug. After about 10 to 20 days of release testing the 10 ml daily samples may be very dilute and begin to register below the 1.0 µg drug per ml buffer when analyzed. If this is the case the amount of buffer can be reduced to 5 ml for the one day release.

Example 15

This example details the analysis methodology for determining the amount of Latanoprost in the drug release samples by HPLC.
Apparatus:
A liquid chromatographic system equipped described below, or the equivalent:
Pump: TSP Spectra Series P4000
Auto Sampler: TSP Spectra Series AS3000
Detector: TSP Spectra Series UV1000
Data Processing Atlas Data Handling System
A Cadenza CD-C18 column, 30 mm×4.6 mm ID, 3 µm size (Imtakt Cat. #CD001
Reagents:
Acetonitrile, Fisher; Cat. #A998-4
Polysorbate 80 (ITC), NOF Corp.
Phosphate Buffer @pH 7.2, Fluka; Cat. #319252-2L
Water, DI Grade
Standards:
Latanoprost Reference Standard
Mobile Phase Preparation:
Mobile Phase A:
Mix 600 mL of water and 400 mL of Acetonitrile. Filter and degas prior to use.
Mobile Phase B:
Mix 250 mL of water and 750 mL of Acetonitrile. Filter and degas prior to use.
Instrument Conditions:
Column: Cadenza CD-C18 column, 30 mm×4.6 mm, 3 µm
Column Temperature: 50° C.
Sample Temperature: Ambient
Detector: 220 nm
Injection Volume: 100 µL
Flush Solvent Mobile Phase A
Flow Rate: 1.0 mL/minute
Mobile Phase Program: 70% Mobile Phase A: 30% Mobile Phase B isocratic
Retention Times Latanoprost About 2.3 minutes
Run Time About 10 minutes

Example 16

Figure 23:
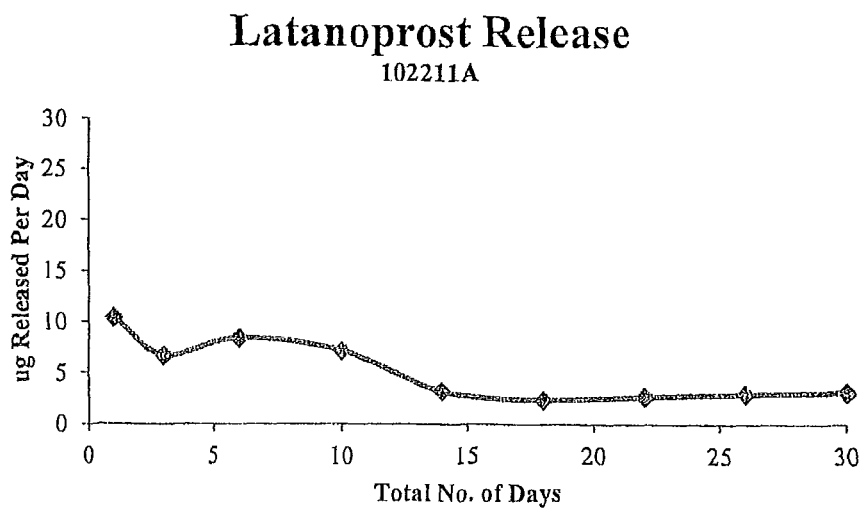
FIG. 23 is a schematic showing a release of latanoprost over a period of time from one exemplary drug delivery device.

This Example details the Latanoprost release kinetics derived from in vitro testing of the drug delivery device of Example 8 wherein the drug release is from the anterior surface of the device. The in vitro drug release testing methodology described in Example 14 was utilized to generate release samples from this device over a one month time period. These samples were analyzed for Latanoprost concentration by the HPLC methodology described in Example 15. The release profile of the release of Latanoprost is presented in FIG. 23. For this example, weight of drug core: 0.0033 gm and Latanoprost content of drug core: 330 µg.

Example 17

Figure 24:
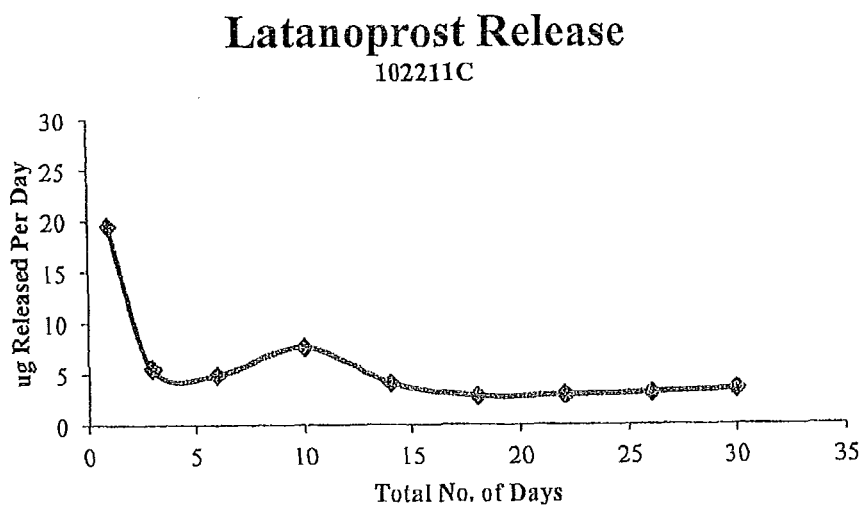
FIG. 24 is a schematic showing a release of latanoprost over a period of time from one exemplary drug delivery device.

This Example details the Latanoprost release kinetics derived from in vitro testing of the drug delivery device of Example 10 wherein the drug release is from the posterior surface of the device. The in vitro drug release testing methodology described in Example 14 was utilized to generate release samples from this device over a one month time period. These samples were analyzed for Latanoprost concentration by the HPLC methodology described in Example 15. The release profile of the release of Latanoprost is presented in FIG. 24. In this example, weight of drug core: 0.0032 gm and Latanoprost content of drug core: 320 µg.

Example 18

Figure 25:
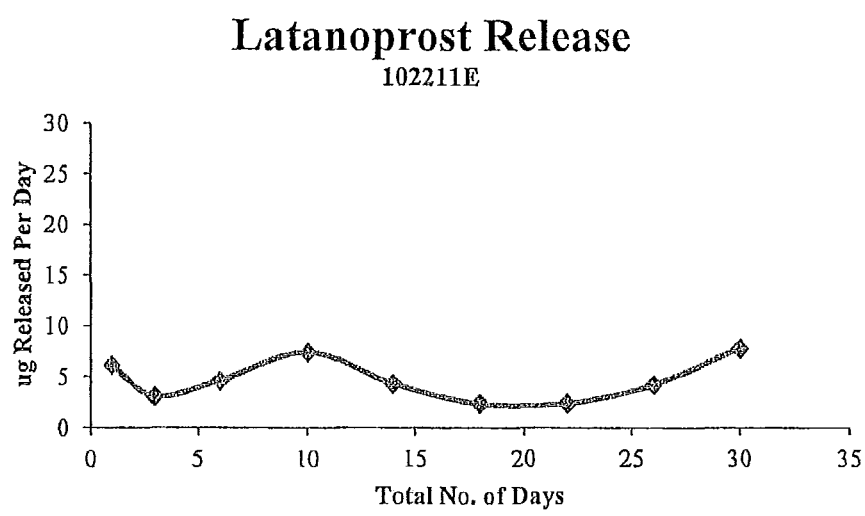
FIG. 25 is a schematic showing a release of latanoprost over a period of time from one exemplary drug delivery device.

This Example details the Latanoprost release kinetics derived from in vitro testing of the drug delivery device of Example 12 wherein the drug release is from the anterior surface of the device. The in vitro drug release testing methodology described in Example 14 was utilized to generate release samples from this device over a one month time period. These samples were analyzed for Latanoprost concentration by the HPLC methodology described in Example 15. The release profile of the release of Latanoprost is presented in FIG. 25. In this example, the weight of drug core: 0.0035 gm and Latanoprost content of drug core: 350 µg.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A method for forming an ocular drug delivery device comprising the steps of:
   forming a drug core containing an active agent;
   disposing an amount of a first material in a first mold part;
   placing the drug core within the first mold part such that the drug release surface is in contact with the first material, wherein the drug core has a barrier disposed on all surfaces thereof except for a drug release surface thereof which is left free of the barrier, the barrier being formed of a material through which the active agent is prevented from diffusing;
   at least partially adhering the drug core to the first material;
   disposing an amount of a second material between the first mold part and an opposing second mold part such that the second material surrounds the drug core and fills a mold cavity between the first and second mold parts, wherein the second polymeric material surrounds and is contact with the barrier of the drug core but is free of contact with the drug release surface of the drug core; and
   polymerizing the second material to form a body of the ocular drug delivery device which is then removed from the first and second mold parts, the ocular drug delivery device body including a drug release membrane, formed of the first material, that covers the drug release surface of the drug core and is configured to permit drug to pass therethrough over a period of time.

2. The method of claim 1, wherein the drug core comprises a cylindrical shaped body formed of a polymeric matrix and the active agent.

3. The method of claim 2, wherein a material that is part of the polymeric matrix, the first material and the second material are the same material.

4. The method of claim 3, wherein the polymer in the polymeric matrix, the first material and the second material are silicone.

5. The method of claim 1, wherein each of the first material and the second material is a material selected from the group consisting of a monomeric material, an oligomeric material, and a resin.

6. The method of claim 1, wherein the step of forming the drug core comprises the steps of:
   mixing one of a monomer, oligomer, and resin with the active agent to form a first mixture;
   disposing the first mixture on a planar surface to form a first material layer; and
   forming the drug core from the first material layer, the drug core having a predetermined shape.

7. The method of claim 6, wherein the drug core is formed from the first material layer by a punch process.

8. The method of claim 1, wherein the amount of the first material comprises an amount that is sufficient such that when the drug core is placed in contact therewith, the first material entirely covers the drug release surface of the drug core so as to form the drug release membrane.

9. The method of claim 8, wherein the drug release membrane has an least substantially uniform thickness across the drug release surface of the drug core.

10. The method of claim 1, wherein the step of adhering the drug core to the first material comprises the step of at least partially polymerizing the first material comprises polymerizing the first material until it is at least tacky and the drug core is at least substantially held in place.

11. The method of claim 1, wherein the drug delivery device is defined by a body that has an anterior surface and an opposite posterior surface which is configured to fit the eye, the drug release membrane being located along the posterior surface.

12. The method of claim 11, wherein the posterior surface includes a base curve that is configured to fit a sclera of the eye to allow the body to be held thereon by fluid attraction.

13. The method of claim 1, wherein the active agent is a prostaglandin.

14. The method of claim 1, wherein the drug core is formed by a casting process.

15. The method of claim 1, wherein the drug delivery device is defined by a body that has a convex shaped anterior surface and an opposite concave shaped posterior surface that is configured to fit and be held on the sclera of the eye, the drug release membrane being located along the anterior surface.

16. A method for forming an ocular drug delivery device for delivery of a therapeutic agent to the eye, the ocular drug delivery device including a preformed body having an anterior surface and an opposite posterior surface for placement on the sclera of the eye, the posterior surface having a preformed curved shape outside of the eye that is defined by a base curve shaped to fit the sclera, the method comprising the steps of:
   forming a first drug core containing an active agent, the first drug core having a drug release surface;
   forming a barrier about the first drug core except for the drug release surface which is free of the barrier, the barrier being formed of a material through which the active agent is prevented from diffusing;

forming a drug release membrane adjacent and in contact with at least a substantial portion of the drug release surface; and forming a remaining part of the device body by an overcast process in which a material is disposed over the first drug core and is polymerized and in combination with the drug release membrane defines the ocular drug delivery device surrounding the drug core.

17. The method of claim 16, wherein the step of forming the drug release membrane comprises the step of inserting a first polymerizable material into a first mold and inserting the first drug core into the first mold such that the drug release surface is in contact with the first polymerizable material; and wherein the step of forming the remaining part of the device body comprises the steps of:

mating a second mold with the first mold; and injecting a second polymerizable material between the first and second molds and polymerizing the second polymerizable material.

18. The method of claim 17, wherein the first and second polymerizable materials are the same.

19. The method of claim 17, wherein the barrier is configured to prevent the active agent from diffusing therethrough, and wherein the first drug core is associated with one of the first and second molds parts and the device includes a second drug core associated with the other of the first and second mold parts such that the drug release membrane covering the first drug core is located along one of the anterior and posterior surfaces of the body and a drug release membrane covering the second drug core is located along the other of the anterior and posterior surfaces of the body.

20. A method for forming an ocular drug delivery device comprising the steps of:

forming a drug core containing an active agent;

forming a barrier about the drug core leaving at least one drug release surface of the drug core free of the barrier, the barrier being formed of a material through which the active agent is prevented from diffusing;

disposing an amount of a first material in a first mold part;

placing the drug core within the first mold part such that the drug release surface is in contact with the first material;

causing the drug core to at least partially adhere to the first material; and forming a remaining body of the device body by an overcast process in which a polymerizable material is disposed over the first drug core and is polymerized and in combination with the drug release membrane defines the body of the ocular drug delivery device surrounding the drug core.

21. The method of claim 20, wherein the second polymeric material surrounds and is contact with the barrier of the drug core but is free of contact with the drug release surface of the drug core.

22. The method of claim 20, wherein the step of causing the drug core to at least partially adhere to the first material comprises the step of at least partially polymerizing the first material.

23. The method of claim 1, wherein the barrier comprises a barrier thin film formed about the drug core.

24. The method of claim 16, wherein the step of forming the barrier about the first drug core comprises the step of forming a thin film by a chemical vapor deposition process.

25. The method of claim 20, wherein the step of forming the barrier about the first drug core comprises the step of forming a thin film by a chemical vapor deposition process.

* * * * *